US 7,547,529 B1

(12) United States Patent
Yabuta et al.

(10) Patent No.: US 7,547,529 B1
(45) Date of Patent: Jun. 16, 2009

(54) METHODS FOR REDUCING THE FORMATION OF BY-PRODUCTS IN THE PRODUCTION OF RECOMBINANT POLYPEPTIDES

(75) Inventors: Masayuki Yabuta, Gunma (JP); Toshihiro Sawano, Tochigi (JP); Yumiko Masuda, Gunma (JP); Kazuhiro Ohsuye, Gunma (JP)

(73) Assignee: Asubio Pharma Co., Ltd., Tokyo (JP)

( * ) Notice: Subject to any disclaimer, the term of this patent is extended or adjusted under 35 U.S.C. 154(b) by 0 days.

(21) Appl. No.: 10/030,452

(22) PCT Filed: May 10, 2001

(86) PCT No.: PCT/JP01/03909

§ 371 (c)(1),
(2), (4) Date: Jan. 10, 2002

(87) PCT Pub. No.: WO01/85945

PCT Pub. Date: Nov. 15, 2001

(30) Foreign Application Priority Data

May 10, 2000 (JP) ............................. 2000-137228

(51) Int. Cl.
  *C12P 21/02* (2006.01)
(52) U.S. Cl. ..................................... 435/71.1; 435/71.2
(58) Field of Classification Search ................ 435/69.1; 514/2, 12; 530/300, 350
See application file for complete search history.

(56) References Cited

U.S. PATENT DOCUMENTS

| 4,987,070 A | | 1/1991 | Magota et al. |
| 5,169,772 A | * | 12/1992 | Zimmerman et al. ........ 435/232 |
| 5,599,690 A | | 2/1997 | Fenton et al. |
| 5,622,845 A | | 4/1997 | Brunner et al. |
| 5,670,340 A | * | 9/1997 | Yabuta et al. ............... 435/69.4 |
| 5,698,418 A | | 12/1997 | Brunner et al. |
| 2003/0170811 A1 | * | 9/2003 | Ueda et al. ................. 435/69.1 |

FOREIGN PATENT DOCUMENTS

| EP | 0164273 A2 | | 12/1985 |
| EP | 0683233 A2 | | 11/1995 |
| GB | 2180539 A | * | 3/1987 |
| JP | 61119189 | | 6/1986 |
| JP | 62044198 | | 2/1987 |
| JP | 687788 | | 1/1989 |
| JP | 2879063 | | 6/1991 |
| WO | WO 90/10706 | | 9/1990 |

OTHER PUBLICATIONS

Power et al., Manual of BBL Products and Laboratory Procedures, six edition, 1988. pp. 1-3 as attached.*
Atlas et al., handbook of Microbiological Media, second edition, 1997. pp. 1-2 as attached.*
Schreiner et al., "Metabolism of methionine and methionine hydroxy analogue by porcine kidney fibroblasts," The Journal of Nutrition, Sep. 1987, vol. 117, No. 9, pp. 1541-1549.
Supplementary European Search Report dated Jul. 22, 2004 for European Application No. 01930035.9-1212-JP0103909.
Burnell et al., "Sulphur metabolism in *Paracoccus denitrificans*. Purification, properties and regulation of serine transacetylase, O-acetylserine sulphydrylase and beta-cystathionase." Biochimica et Biophysica, 1977, vol. 481, pp. 246-265.
Leu et al. "Kinetic mechanism of serine transacetylase from *Salmonella typhimurium*." Biochemistry, 1994, vol. 33, pp. 2667-2671.
European Patent Office Examination dated Dec. 23, 2004 for European Application No. 01930035.9-1212.
Tsai, Larry B. et al., "Control of Misincorporation of *De Novo* Synthesized Norleucine into Recombinant Interleukin-2 in *E. Coli*," Biochemical and Biophysical Communications, 156(2):733-739 (1988).
Bogosian, George, "Biosynthesis and Incorporation into Protein of Norleucine by *Escherichia coli*," The Journal of Biological Chemistry, 264(1):531-539 (1989).
Apostol, Izydor, et al., "Incorporation of Norvaline at Leucine Positions in Recombinant Humah Hemoglobin Expressed in *Escherichia coli*," The Journal of Biological Chemistry, 272(46):28980-28988 (1997).
Kangawa, Kenji, et al., "Purification and Complete Amino Acid Sequence of $\alpha$-Human Atrial Natriuretic Polypeptide ($\alpha$-hANP)," Biochemical and Biophysical Research Communications, 118(1):131-139 (1984).
Masaki, Takeharu: et al., "Studies on a New Proteolytic Enzyme from *Achromobacter Lyticus* M4971 II. Specificity and Inhibition Studies of *Achromobacter* Protease 1," Biochimica et Biophysica Acta, 660:51-55 (1981).
Neidhardt, Frederick C., et al., "Chemical Composition of *Escherichia coli*," *Escherichia coli* and *Salmonella* Cellular and Molecular Biology, vol. I, pp. 13-16, ASM Press, Washington, DC (1996).
Twigg, Andrea J., et al., "Trans-Complementiable Copy-Number Mutants of Plasmid ColE 1," Nature, 283:216-218 (1980).
Kredich, Nicholas M., "Biosynthesis of Cysteine," *Escherichia coli* and *Salmonella* Cellular and Molecular Biology, vol. I, pp. 514-527, ASM Press, Washington, DC (1996).

* cited by examiner

*Primary Examiner*—Suzanne M. Noakes
(74) *Attorney, Agent, or Firm*—Hunton & Williams LLP

(57) ABSTRACT

A method for reducing the formation of a byproduct polypeptide containing an O-acetylserine residue in place of a serine residue by adding at least one of histidine, methionine or glycine to the medium in a method for producing a polypeptide containing a serine residue by culturing transformed cells, and a method for producing a polypeptide containing a serine residue by culturing transformed cells, characterized by reducing the formation of a byproduct polypeptide containing an O-acetylserine residue in place of a serine residue by adding at least one of histidine, methionine or glycine to the medium.

13 Claims, 3 Drawing Sheets

METHODS FOR REDUCING THE FORMATION OF BY-PRODUCTS IN THE PRODUCTION OF RECOMBINANT POLYPEPTIDES

This application is National Stage filing of PCT/JP01/03909 filed May 10, 2001, which claims priority to JP 137228/2000, filed May 10, 2000.

TECHNICAL FIELD

The present invention relates to methods for reducing the formation of byproducts in the production of polypeptides by genetic engineering techniques and methods for producing recombinant polypeptides characterized by reducing the formation of byproducts.

BACKGROUND ART

Genetic engineering techniques are frequently used in the production of physiologically active polypeptides. Basically, genetic codes are normally very faithfully translated, but sometimes an amino acid or an amino acid derivative which does not correspond to the codon table is incorporated into the polypeptides during translation. For example, the percentage of ribosomal mRNA mistranslation was $10^{-4}$ per codon from the experiment of [$^{35}$S]Cys incorporation into highly purified cysteine-free *E. coli* flagellin protein. However, probability of cysteine incorporation into this protein greatly increases in the presence of an antibiotic streptomycin; this is probably because Cys codons (UGU and UGC) are mistranslated for Arg codons (CGU and CGC) (Voet and Voet, Biochemistry, Vol. 2, second edition, Tokyo Kagaku Dojin. pp. 869-870, 1998).

Tsai et al. reported that norleucine is incorporated with high frequency into the location that should naturally be occupied by methionine in the expression of human IL-2 in *E. coli*. (Tsai, L. B. et al., Biochem. Biophys. Res. Commun., Vol. 156, pp. 733-739, 1988). A similar report is found in the expression of bovine somatotropin (Bogosian, G. et al., J. Biol. Chem., Vol. 264, pp. 531-539, 1989). In both cases, the authors assume that norleucine was synthesized in cells by the activation of the leucine synthetic pathway in *E. coli* and added to methionine tRNA in place of methionine, and thus incorporated into the expressed proteins.

In addition to misincorporation of norleucine, Apostol et al. shows that norvaline was misincorporated into the location that should be occupied by leucine in the production of recombinant hemoglobin by *E. coli* (Apostol I. et al., J. Biol. Chem., Vol. 272, pp. 28980-28988, 1997). In this case, the authors also assume that the activation of the leucine synthetic pathway in *E. coli* led to the production of norvaline, which was then incorporated in place of leucine.

As for the above case in which norleucine is incorporated into intended polypeptides in place of methionine, a method for reducing the incorporation of norleucine in heterologous polypeptides expressed in transformed microorganisms grown in a medium by increasing the concentration of methionine and/or leucine or decreasing the amount of norleucine in the fermentation medium or combining both has been known (Japanese Patent No. 2879063, U.S. Pat. No. 5,599,690).

The present inventors investigated a method for efficiently producing human atrial natriuretic peptide (hereinafter also referred to as hANP, the amino acid sequence shown in SEQ ID NO: 1; Kangawa, K. et al., Biochem. Biophys. Res. Commun., Vol. 118, pp. 131-139, 1984) by genetic engineering using *E. coli* as a host cell, and succeeded in constructing a method for efficiently producing hANP from a fusion protein (Japanese Patent No. 1963624). In this method, the fusion protein comprises a protective peptide consisting of the N-terminal 97 amino acids of *E. coli* β-galactosidase, a linker sequence of 3 amino acid residues including a lysine residue (Gln-Phe-Lys) and hANP, and the gene for this fusion protein is encoded on a pBR322-derived expression vector. Transcription of the fusion protein gene is controlled by an *E. coli*-derived lactose promoter, and the expressed fusion protein accumulates as inclusion bodies in *E. coli*. The resulting fusion protein is solubilized by a denaturing agent and then treated with a protease specifically recognizing and cleaving the lysine residue, API (Achromobacter protease I [Masaki, T. et. al., Biochim. Biophys. Acta. Vol. 660, pp. 51-55, 1981]) to release hANP, which is purified by chromatography to give a final product hANP.

During studies of this hANP production process, the present inventors found an impurity that has similar physiochemical properties to those of hANP and cannot be easily separated by chromatography. This impurity is detected as a substance eluting slightly after hANP in analytical reverse phase high-pressure liquid chromatography (RP-HPLC) and exists in a proportion of about 5% to hANP cleaved by enzymatic reaction (this impurity byproduct polypeptide will be hereinafter referred to as R1). This R1 was hard to separate as its elution peak overlapped the tail portion of hANP elution curve in preparative HPLC used on a production scale.

As hANP is used as a medicine for treating acute heart failure, it is important to provide hANP with high purity for such a medical use. Current production processes sufficiently ensure the medical level of purity, but have a problem in production costs because the byproduct polypeptide R1 must be removed during the purification step at the expense of a yield loss. Thus, it has been an important challenge to find a means for reducing the formation of the impurity in the production of high-purity hANP.

In the production of recombinant polypeptides, impure byproducts must be removed during the purification step at the expense of a yield loss leading to a possible problem in production costs, and it is important to find a means for reducing the formation of the byproducts in the production of high-purity recombinant polypeptides. Therefore, an object of the present invention is to provide a method for reducing the formation of byproducts in the production of a polypeptide and a method for producing a recombinant polypeptide characterized by reducing the formation of byproducts.

DISCLOSURE OF THE INVENTION

The present invention provides a method for reducing the formation of a byproduct polypeptide containing an O-acetylserine residue in place of a serine residue by adding at least one of histidine, methionine or glycine to the medium in a method for producing a polypeptide containing a serine residue by culturing transformed cells.

The present invention also provides a method for producing a polypeptide containing a serine residue by culturing transformed cells, characterized by reducing the formation of a byproduct polypeptide containing an O-acetylserine residue in place of a serine residue by adding at least one of histidine, methionine or glycine to the medium.

THE MOST PREFERRED EMBODIMENTS OF THE INVENTION

(1) Identification of Impurity R1

Figure 1:
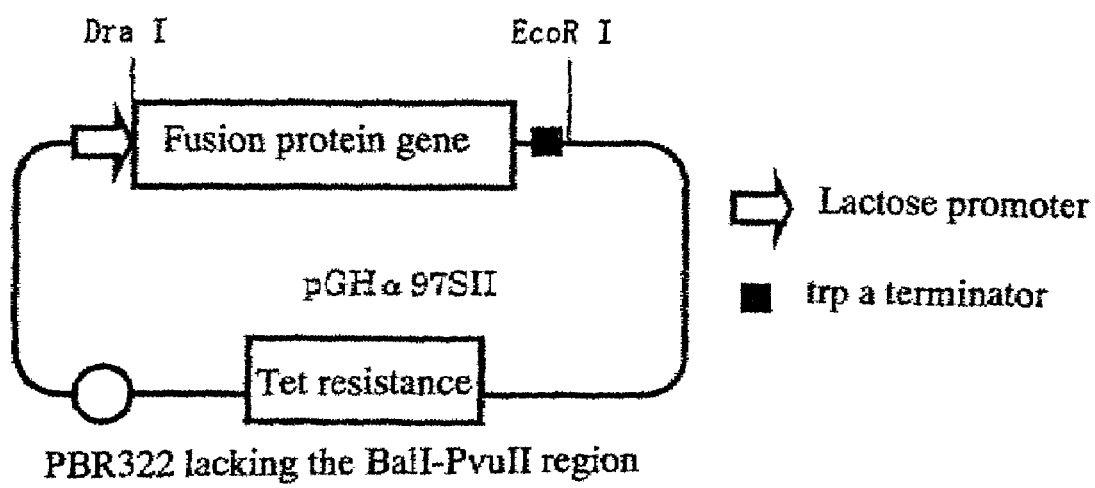
FIG. 1 shows a schematic view of the expression vector pGHα97SII.

In order to analyze the above impurity produced during the production process of hANP, we collected an R1 peak by analytical C18 reverse phase high-pressure liquid chromatography and analyzed its structure by mass spectrometry and amino acid sequencing. The results showed that R1 has a molecular weight greater by 42 than that of hANP. Amino acid sequencing of R1 revealed that it has the same amino acid sequence as that of hANP, indicating that R1 was not produced by replacement of an amino acid in hANP by another amino acid but a derivative of hANP containing a modified amino acid.

If a plurality of modification sites existed, a number of derivatives should appear from combinations thereof, but only a single peak was actually obtained by analytical HPLC, indicating that only one modification site exists. The modification seems to be acetylation in view of the modification reaction occurring during biosynthesis and the molecular weight of 42.

As for the acetylation site, the amino acid sequence of hANP implies the possibility of modification at serine, arginine and tyrosine residues. At first, C-terminal amino acid analysis of the single C-terminal tyrosine residue of hANP showed that the C-terminal amino acid of R1 is tyrosine and denied the possibility of modification at the tyrosine residue. The arginine residue may be less likely to be modified because R1 is also properly cleaved with a protease specifically recognizing arginine (trypsin). Thus, we concluded that acetylation occurred at the serine residue because the acetylation product of serine O-acetylserine residue was shown to be synthesized in cells and may be incorporated in place of the serine residue during translation into the polypeptide. Moreover, R1 could be detected from the point when hANP was released from the fusion protein, which also indicates that R1 should be produced during translation into the polypeptide. This led to the conclusion that the modification in R1 occurred during the expression of the fusion protein but not during the purification step.

(2) Reduction of the Formation of Impurity R1

We attempted to reduce the formation of R1 during the cultivation step. There has been no report of such a modification increasing the molecular weight by 42 in the production of a recombinant peptide in E. coli as a host cell, and therefore, nothing has been known about the means for reducing the formation of R1. We focused on amino acids as constituents of proteins and tried to reduce the formation of R1 by adding an amino acid to the medium to inhibit biosynthesis of the amino acid and thus to reduce the formation of biosynthetic intermediates such as O-acetylserine.

Evaluations were made by culturing hANP-producing cells in the presence of any one of 18 amino acids (L-alanine, glycine, L-leucine, L-isoleucine, L-phenylalanine, L-serine, L-methionine, L-cysteine, L-tryptophan, L-proline, L-glutamine, L-glutamic acid, L-asparagine, L-aspartic acid, L-threonine, L-arginine, L-lysine and L-histidine) and comparing the production levels of hANP and R1.

L-valine was not tested because it induces growth inhibition of cells. L-tyrosine was not tested either, because it seemed to be unsuitable for mass culture due to the low solubility.

The evaluation results showed that addition of glycine, histidine or methionine of the 18 L-amino acids reduced R1 production by 50% or more, revealing that addition of these amino acids significantly reduces R1 production. That is, it was found that addition of these amino acids to the medium reduces R1 production and also increases production levels of inclusion bodies per cell, showing that it is a useful method for mass production of high-purity hANP. The amino acids can be added in an amount that inhibits biosynthesis of the amino acids added (glycine, histidine and/or methionine) in host cells during cultivation. For example, they can be appropriately added to prevent any lack of the amino acid content in the medium monitored during cultivation. Alternatively, the amino acids can be initially added to the medium in an amount sufficient to maintain a necessary amino acid level even at the end of cultivation, after the necessary amino acid level has been preliminarily calculated from the amino acid composition of the host cell (see Frederick C. H. et al., Chemical Composition of *Escherichia coli* in *Escherichia coli* and *Salmonella*, second edition, ASM press, pp. 13-16), the cell density obtained, the amino acid composition of the protein to be expressed and the expression level.

Although glycine, histidine or methionine was evaluated as a single amino acid in the examples below, it can be sufficiently expected that R1 production will be further reduced by combinations thereof.

We performed these evaluations about hANP production as an example, but impurities giving a molecular weight of +42 may also be very likely to occur in the production of polypeptides including peptides or proteins (especially containing serine) other than hANP by genetic engineering techniques and therefore, the present method can be widely applied to peptides and proteins produced by genetic engineering. Moreover, the present invention can also be expected to reduce possible formation of one or more byproducts having an O-acetylserine residue incorporated into one or more of a plurality of serine residues that may be contained in some peptides or proteins.

Examples of peptides to which the present invention can be applied include A-type natriuretic peptide, B-type natriuretic peptide, bradykinin, big gastrin, calcitonin, calcitonin gene related peptide, corticotropin releasing factor, cortistatin, C-type natriuretic peptide, defensin 1, elafin, α-endorphin, β-endorphin, γ-endorphin, endothelin-1, endothelin-2, big endothelin-1, big endothelin-2, big endothelin-3, enkephalin, galanin, big gastrin, gastric inhibitory polypeptide, ghrelin, glucagon, glucagon-like peptide-1, glucagon-like peptide-2, growth hormone releasing factor, histatin 5, insulin, joining peptide, luteinizing hormone releasing hormone, melanocyte stimulating hormone, midkine, neurokinin A, neuropeptide Y, neurotensin, oxytocin, proadrenomedullin N-terminal 20 peptide, parathyroid hormone, PTH related peptide, peptide histidine-methionine-27, pituitary adenylate cyclase activating polypeptide 38, platelet factor-4, peptide T, secretin, serum thymic factor, somatostatin, urocortin, vasoactive intestinal peptide and derivatives thereof, and examples of suitable proteins include growth hormones and derivatives thereof.

Preferably, the present invention is applied to polypeptides containing a serine residue having a molecular weight of 1000-2000. Polypeptides containing a serine residue are more preferably atrial natriuretic peptides, most preferably human atrial natriuretic peptide.

Any host cells that can be used in processes for producing recombinant polypeptides can be used in the present invention. For example, prokaryotic cells such as bacteria (eg, *Escherichia coli* and *Bacillus subtilis*) and eukaryotic cells such as yeasts (eg, genus *Saccharomyces*) and animal cells (eg, CHO cells) can be used. Host cells are preferably microorganisms including bacteria and yeasts, especially *E. coli*.

That is, the present invention relates to:

a) a method for reducing the formation of a byproduct polypeptide by adding at least one of histidine, methionine or glycine to the medium in a method for producing a recombinant polypeptide by culturing transformed cells, b) a method for producing a recombinant polypeptide by culturing transformed cells, characterized by reducing the formation of a byproduct polypeptide by adding at least one of histidine, methionine or glycine to the medium, c) the method as defined in a) or b) wherein the byproduct polypeptide is a derivative of the recombinant polypeptide having a molecular weight shift by +42, d) the method as defined in a) to c) wherein the byproduct polypeptide is an acetylation derivative, e) the method as defined in a) to d) wherein the recombinant polypeptide has serine in the molecule, f) the method as defined in a) to e) wherein the molecular weight of the recombinant polypeptide is about 1000 to 20000, g) the method as defined in f) wherein the recombinant polypeptide is an atrial natriuretic peptide, h) the method as defined in g) wherein the atrial natriuretic peptide is human atrial natriuretic peptide, i) the method as defined in a) to h) wherein the host cell is a prokaryotic cell or an eukaryotic cell in a method for producing a recombinant polypeptide by culturing transformed cells, j) the method as defined in i) wherein the host cell is a microorganism, and k) the method as defined in j) wherein the microorganism is *E. coli*.

INDUSTRIAL APPLICABILITY

The present invention relates to a method for reducing the formation of a byproduct polypeptide by adding at least one of histidine, methionine or glycine to the medium in a method for producing a recombinant polypeptide by culturing transformed cells, and a method for producing a recombinant polypeptide characterized by reducing the formation of a byproduct polypeptide. Especially, the present invention has the effect of reducing the formation of a byproduct polypeptide containing an O-acetylserine residue in place of a serine residue and makes it possible to provide high-purity recombinant polypeptides at lower production costs than previously.

EXAMPLES

The following examples further illustrate the present invention. Various changes and modifications can be made by those skilled in the art and therefore, the present invention is not limited to the examples but also includes such changes and modifications.

Example 1

Preparation of an Expression Vector

A gene encoding a fusion protein containing a protective peptide consisting of the N-terminal 97 amino acids of *E. coli* β-galactosidase (SEQ ID NO: 2), a linker sequence of 3 amino acid residues including lysine (Gln-Phe-Lys) and hANP (SEQ ID NO: 1) was cloned into the EcoRI-DraI site of pBR322 lacking the BalI-PvuII region (Nature. 1980; 283: 216-8) to prepare the expression vector pGHα97SII (FIG. 1, the gene sequence of the fusion protein not shown). The expression vector was constructed according to a standard protocol.

Example 2

Identification of R1

(1) Culture and Recovery of Inclusion Bodies

The *E. coli* strain W3110 harboring the above expression plasmid (W3110/pGHα97SII) was cultured in NU medium shown in Table 1 using a jar fermenter.

TABLE 1

| Composition of NU medium (per L of medium) | |
|---|---|
| Yeast extract | 4 g |
| Potassium dihydrogenphosphate | 4 g |
| Dipotassium hydrogenphosphate | 4 g |
| Disodium hydrogenphosphate | 2.8 g |
| Ammonium chloride | 0.2 g |
| Ammonium sulfate | 1.2 g |
| $MgSO_4/7H_2O$ | 2 g |
| $FeSO_4/7H_2O$ | 40 mg |
| $CaCl_2/2H_2O$ | 40 mg |
| $MnSO_4/nH_2O$ | 10 mg |
| $AlCl_3/6H_2O$ | 10 mg |
| $CoCl_2/6H_2O$ | 4 mg |
| $ZnSO_4/7H_2O$ | 2 mg |
| $Na_2MoO_4/2H_2O$ | 2 mg |
| $CuCl_2/2H_2O$ | 1 mg |
| $H_3BO_4$ | 0.5 mg |
| Tetracycline hydrochloride | 2 mg |

The incubation conditions involved a glucose concentration of 4.5%, 33° C., pH 7.0 and a dissolved oxygen level of 30%, and the pH and the dissolved oxygen level were controlled by dropwise addition of aqueous ammonia and increasing the spinning speed, respectively. After glucose was consumed, glycerol was sequentially added as a carbon source to induce the expression of the hANP fusion protein at an incubation temperature controlled at 37° C. for about 30 hours. Formation of inclusion bodies was observed in cultured cells and the expressed fusion protein corresponded to 30% or more of the total cellular protein.

After incubation, the culture was homogenized with a Manton-Gaulin homogenizer (15M-8AT) at 500 Kg/cm$^2$ and centrifuged to recover precipitated fractions (inclusion bodies). Then, the culture was suspended in an equivalent amount of 30 mM Tris-HCl (pH 9.3) buffer and then centrifuged again to recover precipitate. This washing operation was repeated once again, and the final precipitate was suspended in an appropriate amount of 30 mM Tris-HCl (pH 9.3) buffer.

(2) Detection of R1

Figure 2:
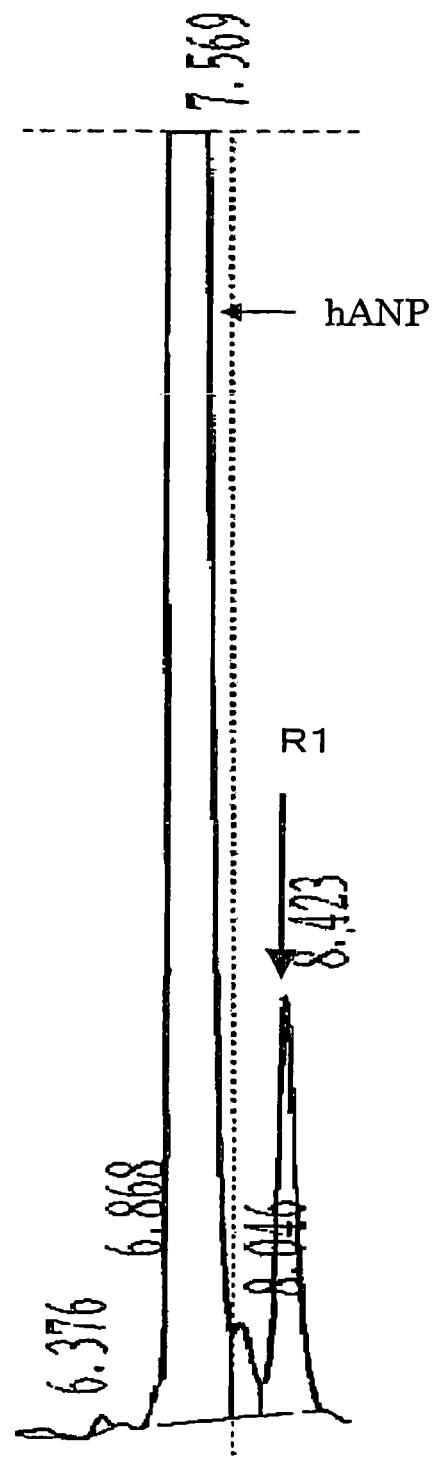
FIG. 2 shows the results of reverse phase HPLC analysis of hANP cleaved from the fusion protein after completion of an enzymatic reaction.

Then, the inclusion bodies were suspended/dissolved in 30 mM Tris-HCl (pH 9.3) buffer containing 5 M urea. The inclusion bodies were used in an amount that gives an OD660 value of 220 when they were suspended in water. To this solution of inclusion bodies was added 3.5 units/L API (Wako Pure Chemical Industries, Ltd.) for cleavage reaction at 30° C. for 1.5 hours. FIG. 2 shows reverse phase HPLC analysis of hANP cleaved after completion of the enzymatic reaction. The analysis was performed at a column temperature of 40° C. by gradient elution with a mixed solution (1:1) of solution A: trifluoroacetic acid solution (1→1000) and solution B: acetonitrile/trifluoroacetic acid solution (0.95→1000) at a flow rate of 1 ml/min, in which solution B was constantly increased from an initial concentration of 43% to a final concentration of 52% over 16 minutes. R1 was detected as an impurity at a relative elution time of 1.1 as compared with hANP.

(3) Purification of R1

Then, R1 was purified for structural analysis of R1. After completion of the enzymatic treatment, the reaction solution was adjusted to pH 5.0 with acetic acid and the protective peptide was precipitated, and then the precipitate was removed by centrifugation. Then, the supernatant was added to a CM-Toyopearl column (TOSOH) equilibrated with 50 mM ammonium acetate solution (pH 5.0) containing 2.5 M urea to adsorb R1 and hANP, and then eluted with a salt concentration gradient of sodium chloride and fractions containing hANP and R1 were collected.

Thus obtained fractions were combined with acetic acid in an amount equivalent to 20% (vol/vol) and passed through a reverse phase column (soken ODS) using octadecyl (C18) as a ligand to adsorb hANP to the column, and then hANP was eluted with acetonitrile gradient and fractions containing hANP and R1 were collected.

Thus obtained fractions were applied to an analytical reverse phase HPLC column (YMC-Pack ODS-A-302: 4.6 mm×150 mm) and peaks for R1 were collected to give high-purity R1.

(4) Structural Analysis of R1

Figure 3:
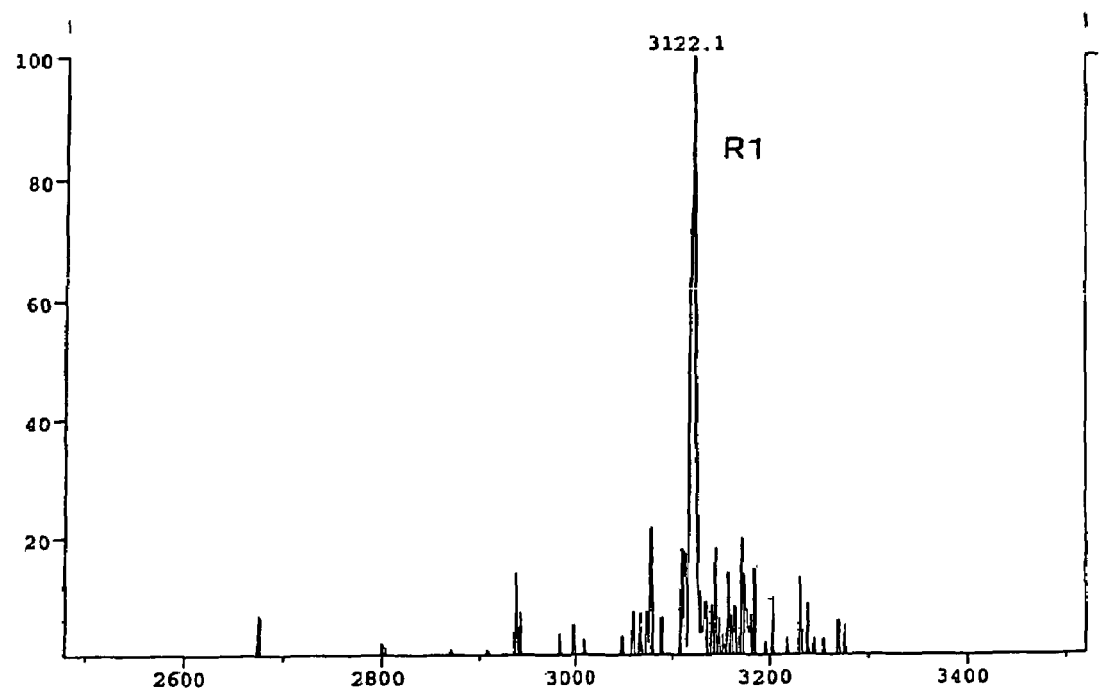
FIG. 3 shows the results of structural analysis of R1 by mass spectrometry.

Structural analysis of R1 was performed by Edman N-terminal amino acid sequencing and mass spectrometric molecular weight analysis (electrospray ionization). The results showed that the N-terminal sequence agreed with the sequence of hANP. The results of mass spectrometry showed a molecular weight of 3122, which is greater by 42 than the molecular weight of hANP 3080 (FIG. 3). These analytical results suggest that R1 might be some modification of hANP. This modification was assumed to contain an acetyl group because of the molecular weight of +42 and the modification reaction occurring in cells. The amino acid sequence of hANP implies the possibility of modification at serine, arginine and tyrosine residues, especially the serine residue. This is because the acetylation product of serine O-acetylserine is known to be synthesized in cells (Kredich, N. M.: Biosynthesis of cysteine in *Escherichia coli* and *Salmonella*, second edition ASM press, pp. 514-527) and O-acetylserine seems to be incorporated in place of serine during translation into the polypeptide.

Example 3

Addition of Amino Acids and Reduction of R1 Production (1) Culture

Frozen stock cells of W3110/pGHα97SII were inoculated on 100 ml of LBD medium (1% Trypton, 0.5% yeast extract, 1 D-glucose, 0.1 M potassium phosphate buffer [pH 7.0]) and cultured with shaking at 37° C. for about 7 hours. To the resulting culture was added glycerol at a final concentration of 10%, and each 1 mL aliquot was dispensed into 20 vials and frozen for subsequent experiments.

The frozen stock cells were inoculated on 200 mL of NU medium shown in Table 1 (except that it contained glucose (4 g/L) as a carbon source and 0.1 g/L yeast extract at pH 7.2) and cultured with shaking at 33° C. overnight. Cells were collected by centrifugation and washed once with physiological saline (0.9% NaCl) and suspended in an appropriate amount of physiological saline (0.9% NaCl) to attain 7-8 times the initial cell density.

Then, 2 mL of this cell suspension was added to 100 mL of NU medium (except that it contained 0.1 g/L yeast extract and glycerin (10 g/L) as a carbon source at pH 6.9-7.0) containing 3 g/L of any one of L-alanine, glycine, L-leucine, L-isoleucine, L-phenylalanine, L-serine, L-methionine, L-cysteine, L-tryptophan, L-proline, L-glutamine, L-glutamic acid, L-asparagine, L-aspartic acid, L-threonine, L-arginine, L-lysine and L-histidine, and incubated at 37° C. overnight.

(2) Recovery of Inclusion Bodies and Reduction of R1 Production

Cells were harvested from the culture in each flask by centrifugation (7000 rpm, 20 min), and then suspended in 5 ml of deionized water and disrupted with an ultrasonic cell disrupter. Then, inclusion bodies were recovered in precipitated fractions by centrifugation (12000 rpm, 5 min) and suspended in 5 ml of 30 mM Tris-HCl (pH 9.3) buffer, and the suspension was centrifuged again (12000 rpm, 5 min) and the inclusion bodies were washed and concentrated.

Then, the resulting inclusion bodies were suspended/dissolved in 1 mL of 30 mM Tris-HCl (pH 9.3) buffer containing 5 M urea. The inclusion bodies were used in an amount that gives an OD660 value of 22 when they were suspended in water. The reaction solution was reacted with 0.004 units/mL of API protease (Wako Pure Chemical Industries, Ltd.) at 30° C. for about 150 min to release of hANP from the fusion protein. The reaction solution was centrifuged (12000 rpm, 5 min) and 300 μL of the supernatant was combined with 13.5-15.5 μL of 5% acetic acid and diluted in 450 μL of purified water. Precipitates formed during this operation were removed by centrifugation (12000 rpm, 5 min) and the supernatant was analyzed by HPLC (column: YMC-Pack ODS-A302). The concentration of R1 was calculated from the ratio of the peak area to that of hANP.

Table 2 shows production levels of R1 relative to hANP.

TABLE 2

| | Production levels of R1 relative to hANP | |
|---|---|---|
| Amino acid added | Ratio of R1 to hANP (%) | Inclusion bodies produced per unit cells (relative level) |
| None | 8.97 | 1.00 |
| L-Lysine | 6.42 | 1.88 |
| L-Threonine | 5.48 | 1.95 |
| L-Methionine | 4.15 | 1.84 |
| L-Alanine | 5.00 | 1.30 |

TABLE 2-continued

Production levels of R1 relative to hANP

| Amino acid added | Ratio of R1 to hANP (%) | Inclusion bodies produced per unit cells (relative level) |
| --- | --- | --- |
| L-Tryptophan | 10.08 | 0.76 |
| L-Serine | 5.24 | 1.24 |
| L-Glycine | 4.26 | 1.25 |
| L-Histidine | 3.71 | 1.39 |
| L-Isoleucine | 5.90 | 1.22 |
| L-Glutamic acid | 5.57 | 1.68 |
| L-Glutamine | 6.10 | 1.16 |
| L-Arginine | 5.02 | 1.92 |
| L-Aspartic acid | 6.83 | 1.87 |
| L-Asparagine | 6.35 | 1.86 |
| L-Proline | 9.01 | 1.62 |

The results showed that addition of histidine, methionine or glycine of the amino acids tested significantly reduced R1 production as evident from the decrease of R1 production level by 50% or more as compared with control (no amino acid added). It was also shown that addition of these amino acids increased the level of inclusion bodies produced per cell. Among histidine, methionine and glycine all having the effect of reducing R1 production, methionine was found to be the most effective for reducing R1 production because of the least production level of R1 relative to hANP coupled to a high production level of inclusion bodies.

However, L-leucine, L-phenylalanine and L-cysteine lowered the expression of the fusion protein to fail in recovery of inclusion bodies, showing that addition of these amino acids is not effective for hANP production.

The invention claimed is:

1. A method for producing a polypeptide comprising a serine residue comprising:
   (i) culturing, in a medium, transformed host cells that produce a recombinant atrial natriuretic peptide comprising a serine residue and a byproduct polypeptide comprising an O-acetylserine residue in place of a serine residue in the atrial natriuretic peptide;
   (ii) adding at least 3 g/L methionine and at least one of at least 3 g/L histidine or at least 3 g/L glycine to the medium; and
   (iii) reducing the formation of said byproduct polypeptide, wherein the formation of said byproduct polypeptide is reduced in an amount greater than or equal to 50% as compared to a control medium with no methionine, histidine, or glycine added.

2. The method of claim 1, wherein the host cell is a prokaryotic cell or an eukaryotic cell.

3. The method of claim 2, wherein the host cell is a microorganism.

4. The method of claim 3, wherein the microorganism is *Escherichia coli*.

5. The method of claim 1, wherein the molecular weight of the polypeptide comprising a serine residue is about 1000 to 20000 daltons.

6. The method of claim 1, wherein the atrial natriuretic peptide is human atrial natriuretic peptide.

7. A method for producing a polypeptide comprising a serine residue comprising:
   (i) culturing, in a medium, transformed host cells that produce a recombinant atrial natriuretic peptide comprising a serine residue and a byproduct polypeptide comprising an O-acetylserine residue in place of a serine residue in the atrial natriuretic peptide;
   (ii) adding at least one of at least 3 g/L histidine or at least 3 g/L glycine to the medium; and
   (iii) reducing the formation of said byproduct polypeptide, wherein the formation of said byproduct polypeptide is reduced in an amount greater than or equal to 50% as compared to a control medium with no histidine or glycine added.

8. The method of claim 7, wherein the host cell is a prokaryotic cell or an eukaryotic cell.

9. The method of claim 8, wherein the host cell is a microorganism.

10. The method of claim 9, wherein the microorganism is *Escherichia coli*.

11. The method of claim 7, wherein the molecular weight of the polypeptide comprising a serine residue is about 1000 to 20000 daltons.

12. The method of claim 7, wherein the atrial natriuretic peptide is human atrial natriuretic peptide.

13. The method of claim 7, further comprising adding an the amount of methionine effective to reduce formation of a byproduct polypeptide wherein said amount is at least 3 g/L.

* * * * *